United States Patent [19]

Mougin et al.

[11] Patent Number: 6,113,882
[45] Date of Patent: Sep. 5, 2000

[54] COSMETIC COMPOSITIONS COMPRISING COPOLYMERS WITH A FLEXIBLE BACKBONE WHICH ARE GRAFTED WITH HYDROPHOBIC AND RIGID MACROMONOMERS

[75] Inventors: Nathalie Mougin, Paris; Bertrand Lion, Livry Gargan; Jean Mondet, Aulnay sous Bois, all of France

[73] Assignee: L'Oreal, Paris, France

[21] Appl. No.: 08/886,024

[22] Filed: Jun. 30, 1997

[30] Foreign Application Priority Data

Jun. 28, 1996 [FR] France .................................. 96 08113

[51] Int. Cl.[7] .............................. A61K 7/06; A61K 7/48; A61K 7/11
[52] U.S. Cl. .............................. 424/47; 424/59; 424/61; 424/70.1; 424/70.11; 424/70.16; 424/70.17; 424/78.02
[58] Field of Search .................................. 424/401, 70.1, 424/59, 70.16, 47, 78.02, 70.11, 70.17, 61

[56] References Cited

FOREIGN PATENT DOCUMENTS

| | | |
|---|---|---|
| 91/15185 | 10/1991 | WIPO . |
| 91/15186 | 10/1991 | WIPO . |
| 91/15187 | 10/1991 | WIPO . |
| 95/01383 | 1/1995 | WIPO . |
| 96/00562 | 1/1996 | WIPO . |

*Primary Examiner*—Jyothsan Venkat
*Attorney, Agent, or Firm*—Finnegan, Henderson, Farabow, Garrett & Dunner, L.L.P.

[57] ABSTRACT

A cosmetic or dermatological composition comprising a graft copolymer having a backbone comprising a copolymer with a glass transition temperature ranging from 0 to 30° C., capable of being obtained by radical polymerization or by polycondensation and comprising on the backbone chain at least one graft unit including a hydrophobic macromonomer with a glass transition temperature higher than 25° C.

32 Claims, No Drawings

COSMETIC COMPOSITIONS COMPRISING COPOLYMERS WITH A FLEXIBLE BACKBONE WHICH ARE GRAFTED WITH HYDROPHOBIC AND RIGID MACROMONOMERS

The present invention relates to the use of copolymers with a flexible backbone which are capable of being obtained by radical polymerization or polycondensation and grafted with rigid and hydrophobic macromonomers, in and for the preparation of cosmetic or dermatological compositions, and to these compositions, and uses thereof.

For many cosmetic applications, especially those intended for the treatment and care of hair, the skin or the eyelashes, polymers are employed which are capable, after application to the substrate to be treated and drying, of forming a deposit which has mechanical properties and film-forming properties. With this in mind, polymers of a hydrophilic nature are sought after, in order to be easily removed under the action of an aqueous solution of surfactants. In parallel, what is sought after is to obtain a hydrophobic deposit at the surface in order, on the one hand, to resist the surrounding moisture, especially a deposit which is not hygroscopic to the touch, a deposit which resists rain (hair-care applications or for the skin), or a deposit which resists tear liquid (mascaras). On the other hand, a hydrophobic deposit is sought after, to contribute cosmetic properties such as softness to the touch, which are generally conferred by hydrophobic substances in cosmetics.

To combine all these characteristics together, polymers of different hydrophilicity and hydrophobicity are generally mixed or else a hydrophobic substance is associated with a hydrophilic polymer. It is generally difficult to control completely the stratification of these mixtures after drying of the deposit to obtain both good mechanical and film-forming properties and a hydrophobic surface.

Another problem relating to film-forming polymers arises in the field of aqueous nail varnishes. In fact, it is often difficult to adapt the properties of the polymer which must quickly form a film at ambient temperature and give a film at the same time exhibiting a high flexibility and good resistance to water while retaining a sufficient surface hardness.

One of the objectives of the present invention is therefore to employ, in cosmetic or dermatological compositions, polymers which have satisfactory film-forming properties, which are hydrophobic at the surface and resistant to the surrounding moisture, and which impart good cosmetic properties such as softness to the touch.

Another objective of the invention is to employ, in and for the preparation of aqueous nail varnishes, film-forming polymers producing a film which at the same time has high flexibility characteristics, which resists water well, and which has a satisfactory surface hardness.

Applicants have surprisingly discovered that these objectives can be attained by employing, in and for the preparation of cosmetic or dermatological compositions, specific graft copolymers in which the backbone is flexible and includes a copolymer capable of being obtained by radical polymerization or by polycondensation, and comprising at least one rigid and hydrophobic macromonomer graft unit on the backbone chain.

Applicants have furthermore discovered that the specific graft copolymers of the invention make it possible to produce aqueous gels exhibiting excellent mechanical and film-forming properties and intended for application to the hair, the skin or the lips.

In fact, the specific graft copolymers of the invention, in particular those which have a water-soluble backbone and rigid hydrophobic graft units, could, in contact with an aqueous medium, give rise to the deposition of an aqueous gel, soft and not sticky to the touch, swelling in water and exhibiting excellent mechanical and film-forming properties. They can in particular be employed in and for the preparation of hair-care products for setting hair, retaining their setting properties in a moist environment. They can also be employed in and for the preparation of hydrating products for the care or makeup of the skin or the lips, capable of containing active substances without giving rise to a sticky deposit.

The subject-matter of the present invention thus includes the use, in and for the preparation of cosmetic or dermatological compositions, of a graft copolymer whose backbone (S) includes a copolymer with a glass transition temperature Tg ranging from 0 to 30° C., capable of being obtained by radical polymerization or by polycondensation and comprising on the backbone (S) chain at least one graft unit containing a hydrophobic macromonomer (M) with a glass transition temperature Tg higher than 25° C.

The present invention also relates to cosmetic or dermatological compositions containing in a cosmetically acceptable medium at least one graft copolymer whose backbone (S) includes a copolymer with a glass transition temperature Tg ranging from 0 to 30° C., capable of being obtained by radical polymerization or by polycondensation and comprising on the backbone (S) chain at least one graft unit containing a hydrophobic macromonomer (M) with a glass transition temperature Tg higher than 25° C.

Other subjects of the invention will appear in light of the description and the examples which follow.

The copolymers of the invention are graft copolymers which are soluble or dispersible in water, the lower ($C_1$–$C_4$) alcohols and mixtures of water and of lower alcohol(s).

A "hydrophobic graft unit" is intended, throughout the text of the description, to mean any water-insoluble graft unit, the lower ($C_1$–$C_4$) alcohols or mixtures of water and of lower alcohol(s).

A "macromonomer" is intended throughout the text of the description to mean any oligomer comprising on one end alone either a group containing ethylenic unsaturation capable of polymerizing by a radical route with monomers forming the backbone (S) of the copolymer of the invention and of being grafted onto the polymer chain of the backbone (S), or a reactive functional group capable of reacting with the monomers (A) and (B) of the backbone (S) or else with the preformed backbone (S).

The macromonomers (M) grafted by covalent bonding onto the polymer chain of the backbone (S) of the copolymers of the invention are preferably chosen from hydrocarbon, hydrofluorocarbon or fluorocarbon macromonomers which have a glass transition temperature Tg higher than 25° C.

The macromonomers (M) have a glass transition temperature Tg which is preferably higher than or equal to 30° C.

The macromonomers (M) are additionally hydrophobic, that is to say insoluble in water and have a surface tension generally lower than or equal to 40 dyne/cm at 20° C.

The macromonomers (M) preferably have a mean molecular weight, measured at the top of a peak using steric exclusion chromatography, ranging from 200 to 30,000.

The macromonomers (M) of the invention are preferably chosen from the group including:

oligomers which can copolymerize by a radical route with the monomers of the backbone (S) and which have on one of the ends thereof an end radical carrying a double bond;

oligomers which have on one of the ends thereof an end radical carrying a reactive functional group capable of interacting with the backbone (S) or the monomers which it includes, such as —OH, —NH$_2$, —COOH or anhydride;

oligomers which can polycondense with the monomers of the backbone (S), which have on one of the ends thereof an end radical carrying a reactive functional group capable of taking part in a polycondensation, such as a diol, diamine or dicarboxylic acid.

The macromonomers (M) of the invention can also be polycondensate oligomers, for example of the polyester, polyamide or polyurethane type.

Among the macromonomers (M) grafted onto the copolymers of the invention there may preferably be mentioned:

(a) polystyrene macromonomers of Tg higher than 25° C. and which have an end group containing ethylenic unsaturation (methacrylate, acrylate, styrene, etc.) or a reactive functional end group capable of interacting with the backbone (S) or the monomers which it includes or a reactive functional end group capable of taking part in a polycondensation, such as a diol, diamine or dicarboxylic acid, among which there may be mentioned in particular polystyrene macromonomers and substituted polystyrene macromonomers with a methacrylate, dicarboxyl or dihydroxyl end, such as the products sold by Toa Gosei;

(b) linear or branched $C_1$–$C_{20}$ alkyl acrylate or methacrylate homopolymers and copolymers of Tg higher than 25° C. and which have an end group chosen from vinyl, allyl, methallyl, (meth)acryloyl, ethacryloyl, vinylbenzoyl, vinylbenzyl, $C_1$–$C_4$ alkenyl, $C_1$–$C_6$ cycloalkenyl or an end reactive functional group capable of interacting with the backbone (S) or the monomers which it includes, such as —OH, —NH$_2$, —COOH or anhydride, or a reactive functional end group capable of taking part in a polycondensation, such as a diol, diamine or dicarboxylic acid, among which there may be mentioned in particular poly (methyl methacrylate) macromonomers with a methacrylate, dicarboxyl or dihydroxyl end, such as the products sold by Toa Gosei;

c) polymers or copolymers of fluorinated or perfluorinated monomers, of Tg higher than 25° C. and which have an end group containing ethylenic unsaturation or a reactive functional end group capable of interacting with the backbone (S) or the monomers which it includes or a reactive functional end group capable of taking part in a polycondensation, among which perfluoroalkyl (meth)acrylate homopolymers or copolymers may be mentioned in particular.

The macromonomers (M) are present in the copolymers of the composition of the invention in a proportion which preferably ranges from 1 to 60% by weight, relative to the total weight of the graft copolymer.

The graft copolymers which may be used in accordance with the present invention preferably have a mean molecular weight, measured at the top of a peak using steric exclusion chromatography, ranging from 10,000 to 5,000,000.

The graft copolymers are in general soluble or dispersible in aqueous media or alcoholic or hydroalcoholic media based on lower alcohols. They may be nonionic, anionic, cationic or amphoteric, the ionic groups being preferably situated in the backbone (S) structure, to introduce the hydrophilicity. Latices and pseudolatices may be mentioned among the dispersible copolymers.

The backbone (S) of the copolymers of the invention has a glass transition temperature Tg ranging from 0 to 30° C.

The backbone (S) of the copolymers of the invention includes a copolymer obtained by radical polymerization or by polycondensation.

The backbone (S) obtained by a radical route is preferably a result of the polymerization of:

(a) at least one monomer or mixture of monomers (A) containing ethylenic unsaturation, and optionally (b) at least one polar and hydrophilic monomer or mixture of monomers (B) containing ethylenic unsaturation, the monomers (A) and (B) being chosen such that the glass transition temperature Tg of the backbone (S) varies from 0 to 30° C. The presence of the monomer(s) (B) will depend on the desired cosmetic application.

The monomers of the (A) type are chosen, for example, from the group including:

acrylic or methacrylic esters or amides obtained from linear, branched or cyclic aliphatic alcohols and/or aromatic alcohols, preferably $C_1$–$C_4$, such as methyl (meth)acrylate, ethyl (meth)acrylate, propyl (meth) acrylate, butyl (meth)acrylate, isobutyl (meth)acrylate, tert-butyl (meth)acrylate or tert-butylacrylamide;

vinyl, allyl or methallyl esters or amides obtained from linear, branched or cyclic aliphatic alcohols and/or aromatic alcohols, preferably $C_1$–$C_6$, such as vinyl acetate, vinyl propionate, vinyl benzoate or vinyl tert-butylbenzoate;

olefins such as ethylene, propylene, styrene or substituted styrene;

fluorinated or perfluorinated acrylic or vinyl monomers; and mixtures thereof.

The monomers of the (B) type of the invention are chosen from anionic, cationic, amphoteric or nonionic, hydrophilic and polar monomers containing ethylenic unsaturation, and mixtures thereof.

Among the anionic monomers (B) there may particularly be mentioned:

monomers containing at least one acidic functional group in free form or else in a partially or completely neutralized form, such as monocarboxylic acids like acrylic, methacrylic or crotonic acids, dicarboxylic acids or acid anhydrides and their monoesters or monoamides like maleic anhydride in the form of diacid, of monoester or monoamide or itaconic acid;

monomers containing at least one sulphonic acid functional group in free form or else in a partially or completely neutralized form, such as vinyl- or styrenesulphonic acid or 2-acrylamido-2-methylpropanesulphonic acid;

monomers containing at least one phosphoric or phosphonic acid functional group in free form or else in a partially or completely neutralized form.

The anionic monomers (B) are preferably partially or completely neutralized with a monobasic compound such as an inorganic base like soda or potash, or an amino alcohol, for example taken from the group including 2-amino-2-methyl-1-propanol (AMP), triethanolamine, triisopropanolamine (TIPA), monoethanolamine, tri (2-hydroxy)-1-propylamine, 2-amino-2-methyl-1,3-propanediol (AMPD) and 2-amino-2-hydroxymethyl-1,3-propanediol.

Among the cationic monomers (B) there may particularly be mentioned:

monomers containing an amine functional group in free form or else partially or completely neutralized or else partially or completely quaternized, such as dimethylaminoethyl (meth)acrylate, dimethylaminoethylmethacrylamide, vinylamine, vinylpyridine and diallyldimethylammonium chloride.

The cationic monomers (B) are preferably partially or completely neutralized with an inorganic or organic acid such as hydrochloric, acetic, lactic or glycolic acid or else partially or completely quaternized with an alkyl, cycloalkyl or aryl halide or a dialkyl sulphate (dimethyl or diethyl sulphate).

Among the amphoteric monomers (B) there may be mentioned carboxybetaines or sulphobetaines obtained by partial or complete quaternization of monomers containing ethylenic unsaturation comprising an amine functional group with sodium salts of a carboxylic acid containing labile halide (sodium chloroacetate) or with cyclic sultones (propane sultone).

Among the nonionic monomers (B) there may be mentioned:

$C_1$–$C_4$ hydroxyalkyl (meth)acrylates such as 2-hydroxyethyl (meth)acrylate or 2-hydroxypropyl (meth)acrylate, acrylamides such as methacrylamide and di($C_1$–$C_4$)alkyl (meth)acrylamides;

N-vinylpyrrolidone; and ethylene glycol, diethylene glycol and polyethylene glycol (meth)acrylates containing a hydroxyl or ether end.

The backbone (S) obtained by polycondensation is preferably a result of the reaction of:

(a) at least one polycondensable monomer or mixture of monomers (A') and optionally b) a monomer or mixture of monomers (B') which can polycondense with the monomer(s) (A'), carrying at least one hydrophilic functional group introducing solubility or dispersibility in water, alcoholic media or hydroalcoholic media, the monomers (A') and (B') being chosen such that the glass transition temperature Tg of the backbone (S) varies from 0 to 30° C.

The backbones (S) of the polycondensate type are chosen, for example, from polyesters, polyamides, polyurethanes and polyesteramides preferably containing partially or completely neutralized anionic groups such as carboxylic or sulphonic or partially or completely neutralized or quaternized cationic groups such as tertiary amines. They can also be of polyurethane and/or polyurea nature and contain other types of block, such as polyethers and/or polyesters and containing partially or completely neutralized or quaternized ionic groups.

The graft copolymers which may be used in accordance with the invention can be obtained by direct radical copolymerization of monomers (A) and (B) as defined above constituting the backbone (S) and of a macromonomer (M) which has on one end alone a group containing ethylenic unsaturation which is copolymerizable with the monomers (A) and (B).

The direct radical polymerization can then be done in solution in a common solvent or a mixture of common solvents. It can also be performed in a heterogeneous medium, in particular in suspension or in emulsion in water, the macromonomer being dissolved in the mixture with the monomers (A) and (B) as defined above.

When the backbone (S) is a polycondensate such as a polyester, a polyamide, a polyurethane or a polyesteramide, the graft copolymers in accordance with the invention can be obtained by direct polycondensation of monomers (A') and (B') as defined above constituting the backbone (S) and of a macromonomer (M) which has on one end alone two reactive functional end groups, for example, diol, diamine, dicarboxylic acid or acid anhydride, capable of polycondensing with the monomers (A') and (B').

The direct polycondensation can be carried out in solution, in dispersion or in a melt according to a reaction of the esterification, amidification, transesterification or transamidification type.

Finally, the graft copolymers in accordance with the invention can also be obtained by reacting the copolymer of the backbone (S), synthesized beforehand, with a macromonomer (M) which has an appropriate reactive functional end group capable of interacting with the preferably monofunctional backbone (S), e.g., amine, alcohol, carboxylic acid, anhydride, epoxy etc. The reaction is generally performed in solution or in a melt.

The cosmetic and dermatological compositions according to the invention therefore contain polymers as described above, in a cosmetically acceptable substrate, for applications as varied as those encountered, for example, in the field of hair care, of make-up or else of care of the skin, or of any other cosmetic field in which the use of a film-forming substance is desirable or sought after.

The graft copolymers according to the invention can be employed alone as a film-forming agent or as an additive to conventional film-forming agents in and for the preparation of cosmetic or dermatological compositions.

Among the applications preferably aimed at by the present invention there may be mentioned more particularly, the field of hair-care products (hair washing, care or beauty), where the compositions according to the invention can be in the form of aerosols, of mousse, of shampoos, of aftershampoos, of lotions or of dressing or treating gels, hair fixing sprays or lotions for styling or hairsetting or fixing, the field of make-up products, for example for making up the nails, eyelashes or lips, where the compositions according to the invention can be in the form of a nail varnish, of mascaras or of eyeliners or of lip rouges, and in the field of skin care products (creams, milks, lotions, masks, serums or sun products).

The concentration of graft copolymer in the cosmetic or dermatological compositions of the invention generally ranges from 0.1 to 50%, and preferably from 1 to 30% by weight of the total weight of the composition. It varies according to the envisaged cosmetic or dermatological application.

In the case of nail varnishes this proportion is generally higher than or equal to 30% by weight when the copolymer of the invention is employed alone as a film-forming agent.

The cosmetically acceptable carrier of the compositions according to the invention preferably includes water, one or several cosmetically acceptable organic solvents or a mixture of water and one or several cosmetically acceptable organic solvents.

Among these organic solvents, use is particularly made of the $C_1$–$C_4$ lower alcohols, such as ethanol.

The graft copolymers according to the invention are dissolved or in dispersion in the carrier of the compositions of the invention.

The compositions may additionally and obviously contain various adjuvants intended to make them acceptable in a specific cosmetic application.

In this regard, the compositions according to the invention may contain conventional cosmetic additives chosen from fatty substances such as mineral, vegetable, animal and synthetic oils, animal, fossil, vegetable, mineral and synthetic waxes, organic solvents, thickening agents, emollients, antifoam agents, hydrating agents, moisteners, treatment agents (against hair loss, against dandruff etc.), antiperspirants, alkalifying agents, UV-A or UV-B or broad band sunscreens, dyes, pigments, perfumes, plasticizers, preserving agents, anionic, nonionic or amphoteric organic polymers compatible with the graft copolymers of the invention, and propellent agents when the compositions are in aerosol form.

The person skilled in the art will, of course, take care to choose the optional additional compound(s) mentioned above so that the advantageous properties intrinsically linked with the compositions according to the invention are not, or are substantially not damaged by the envisaged addition(s).

Another subject of the invention is a process for cosmetic treatment of keratinous materials such as the skin, the hair, the scalp, the eyelashes, the eyebrows, the nails or the lips, characterized in that it comprises applying to the latter a composition as defined above.

EXAMPLES

Example of Preparation: Preparation of an Acrylic Copolymer Grafted with Polystyrene Graft Units The backbone (S) was an acrylic acid/isobutyl acrylate/tert-butyl acrylate copolymer. The macromonomer (M) employed was a polystyrene oligomer with a monomethacrylate end of number molecular mass of 6000, sold under the name AS-6 by Toa Gosei Chemicais.

The acrylic graft copolymer was produced from the following composition:

| | |
|---|---|
| tert-Butyl acrylate (A) | 30% by weight |
| Isobutyl acrylate (A) | 50% by weight |
| Acrylic acid (B) | 10% by weight |
| Polystyrene macromonomer containing a monomethacrylate end | 10% by weight |

100 g of the monomer mixture described above were introduced into a reactor with central stirring, a condenser, a thermometer and nitrogen bubbling. Next, 400 g of a solvent mixture consisting of 320 g of tetrahydrofuran and 60 g of toluene were introduced. Stirring was continued at 250 revolutions/minute and with nitrogen bubbling until all the reactants had completely dissolved. They were then heated to reflux of the solvent mixture.

As soon as reflux was reached, 2 g of 97% tertbutylperoxy 2-ethylhexanoate initiator (sold by Akzo under the name Trigonox 21 S) were introduced. These stirring and temperature conditions were maintained for 12 hours. At the end of synthesis the ambient temperature was regained and the reaction mixture was diluted with tetrahydrofuran alone and the polymer was purified by precipitation of the solution into 5 l of petroleum ether. The precipitate was vacuum-dried at a temperature of 50° C. for 48 hours to constant weight.

The acid value of the polymer was 80 (theoretical 77).

The characterization of the molecular weight by steric exclusion chromatography on μ-Styragel columns with tetrahydrofuran eluent against polystyrene standards, gave only 1 main peak corresponding to a molecular weight of 49,500. No trace of free macromonomer was detected.

The glass transition temperature Tg of the backbone, measured by DSC (differential calorimetry) was approximately 10° C.

The glass transition temperature Tg of the macromonomer, measured by DSC (differential calorimetry) was approximately 100° C.

Example of Formulation: Aerosol Styling Hair Fixing Spray

| Composition A: | |
|---|---|
| Graft acrylic copolymer from the example of preparation | 8% by weight (A.S.: active substance) |
| 2-Amino-2-methyl-l-propanol for 100% neutralization | q.s. |
| Ethanol | q.s. 100% by weight |

The composition was dispersed in hot ethanol. After return to the ambient temperature, a stable milky dispersion in ethanol was obtained.

| Pressurization: | |
|---|---|
| Composition A | 70% by weight |
| Dimethyl ether | 30% by weight |

The aerosol hair fixing spray obtained, after application to hair, gave good fixing of the head of hair with good disentangling facility without any sticky feel and was easily removed on shampooing.

What is claimed is:

1. A cosmetic or dermatological composition, said composition comprising in a cosmetically or dermatologicai acceptable carrier, a graft copolymer having a backbone that includes a copolymer with a glass transition temperature Tg ranging from 0 to 30° C., said graft copolymer being obtained by radical polymerization or by polycondensation, and comprising on said backbone at least one graft unit comprising a hydrophobic macromonomer with a glass transition temperature Tg higher than 25° C.

2. The composition according to claim 1, wherein said at least one grafted macromonomer is a hydrocarbon, hydrofluorocarbon or fluorocarbon hydrophobic macromonomer having a glass transition temperature Tg higher than 25° C.

3. The composition according to claim 2, wherein said at least one grafted macromonomer has a glass transition temperature Tg higher than or equal to 30° C.

4. The composition according to claim 1, wherein said at least one grafted macromonomer has a surface tension lower than or equal to 40 dyne/cm at 20° C.

5. The composition according to claim 1, wherein said at least one grafted macromonomer has a mean molecular weight, measured at the top of a peak using steric exclusion chromatography, ranging from 200 to 30,000.

6. The composition according to claim 1, wherein said at least one grafted macromonomer is an oligomer which can copolymerize by a radical route with the monomers of the backbone and which has on one of the ends thereof an end radical carrying a double bond;

an oligomer which has on one of the ends thereof an end radical carrying a reactive functional end group interacting with the backbone or the monomers that make up the backbone; or an oligomer which can polycondense with the monomers of the backbone and which has on one of the ends thereof an end radical carrying a reactive functional end group taking part in a polycondensation reaction.

7. The composition according to claim 6, wherein said at least one grafted macromonomer is a polycondensate oligomer.

8. The composition according to claim 1, wherein said at least one grafted macromonomer is (a) a polystyrene macromonomer and a substituted polystyrene macromonomer having a glass transition temperature Tg higher than 25° C. and having an end group containing ethylenic unsaturation or a reactive functional end group interacting with the backbone or the monomers that make up the backbone or a reactive functional end group taking part in a polycondensation reaction;

(b) a linear or branched $C_1$–$C_{20}$ alkyl acrylate or methacrylate homopolymer and a copolymer having a glass transition temperature T'g higher than 25° C. and having as an end group vinyl, allyl, methallyl, (meth)acryloyl, ethacryloyl, vinylbenzoyl, vinylbenzyl, $C_1$–$C_4$ alkenyl, $C_1$–$C_6$ cycloalkenyl, or a reactive functional end group interacting with the backbone or the monomers making up the backbone or a reactive functional end group taking part in a polycondensation reaction; or (c) a polymer or a copolymer of fluorinated or perfluorinated monomers having a glass transition temperature Tg higher than 25° C. and having an end group containing ethylenic unsaturation or a reactive functional end group interacting with the backbone or the monomers making up the backbone or a reactive functional end group taking part in a polycoridensation reaction.

9. The composition according to claim 1, wherein said at least one grafted macromonomer is present in said composition in a proportion ranging from 1 to 60% by weight relative to the total weight of the graft copolymer.

10. The composition according to claim 1, wherein said graft copolymer has a mean molecular weight, measured at the top of a peak using steric exclusion chromatography, ranging from 10,000 to 5,000,000.

11. The composition according to claim 1, wherein said backbone comprises a copolymer obtained by radical polymerization of:

(a) at least one monomer or mixture of monomer (A) containing ethylenic unsaturation, and optionally (b) at least one polar and hydrophilic monomer or mixture of monomers (B) containing ethylenic unsaturation.

12. The composition according to claim 1, wherein said backbone comprises a copolymer obtained by polycondensation of:

(a) at least one polycondensable monomer or mixture of polycondensable monomers (A') and optionally (b) a monomer or mixture of monomers (B') which can polycondense with said at least one monomer (A') and which carries at least one hydrophilic functional group contributing solubility or dispersibility in water, alcoholic media or hydroalcoholic media, said monomers (A') and (B') being selected so that the glass transition temperature Tg of said backbone varies from 0 to 30° C.

13. The composition according to claim 11, wherein said backbone is a polycondensate which is a polyester, a polyamide, a polyurethane, a polyurea, or a polyesteramide containing partially or completely neutralized anionic groups or partially or completely neutralized or quaternized cationic groups, or a multiblock polycondensate of the polyurethane and the polyurea.

14. The composition according to claim 11, wherein said at least one monomer or mixture of monomers (A) is:

an acrylic or methacrylic ester or amide obtained from a linear, branched or cyclic aliphatic alcohol and/or an aromatic alcohol;

a vinyl, allyl or methallyl ester or amide obtained from a linear, branched or cyclic aliphatic alcohol and/or an aromatic alcohol;

an olefin;

a fluorinated or perfluorinated acrylic or vinyl monomer; or a mixture thereof.

15. The composition according to claim 11, wherein said at least one monomer or mixture of monomers (A) is methyl (meth)acrylate, ethyl (meth)acrylate, propyl (meth)acrylate, butyl (meth)acrylate, isobutyl (meth)acrylate, tert-butyl (meth)acrylate, tert-butylacrylamide, vinyl acetate, vinyl propionate, vinyl benzoate, vinyl tert-butylbenzoate, ethylene, propylene, styrene, substituted styrene, or mixtures thereof.

16. The composition according to claim 11, wherein said at least one monomer or mixture of monomers (B) is a hydrophilic and polar, anionic, cationic, amphoteric, nonionic monomer containing ethylenic unsaturation, or a mixture thereof.

17. The composition according to claim 16, wherein said anionic monomers (B) are:

monomers containing at least one acidic functional group in free form or in a partially or completely neutralized form;

monomers containing at least one sulphonic acid functional group in free form or in a partially or completely neutralized form; or monomers containing at least one phosphoric or phosphonic acid functional group in free form or in a partially or completely neutralized form.

18. The composition according to claim 17, wherein said anionic monomers (B) are monocarboxylic acids, dicarboxylic acids, acid anhydrides, their monoesters or monoamides, vinyl- or styrene-sulphonic acid or 2-acrylamido-2-methylpropanesulphonic acid, said anionic monomers (B) being in free form, a partially neutralized form or a completely neutralized form.

19. The composition according to claim 16, wherein the cationic monomers (B) are:

monomers containing at least one amine functional group in free form, monomers containing at least one amine functional group in a partially or completely neutralized form, or monomers containing at least one amine functional group in a partially or completely quaternized form.

20. The composition according to claim 19, wherein said cationic monomers (B) are:

dimethylaminoethyl (meth) acrylate, dimethylaminoethylmethacrylamide, vinylamine, vinylpyridine, or diallyldimethylammonium chloride, said cationic monomers (B) being in free form, in a partially or completely neutralized form and in a partially or completely quaternized form.

21. The composition according to claim 16, wherein said amphoteric monomers (B) are:

carboxybetaines or sulphobetaines obtained by partial or complete quaternization of monomers containing ethylenic unsaturation comprising an amine functional group with sodium salts of a carboxylic acid containing labile halide or with cyclic sultones.

22. The composition according to claim 16, wherein said nonionic monomers (B) are:

$C_1$–$C_4$ hydroxyalkyl(meth)acrylates;

acrylamides;

N-vinylpyrrolidone;

ethylene glycol (meth)acrylates containing a hydroxy or ether end group;

diethylene glycol (meth)acrylates containing a hydroxy or ether end group; or polyethylene glycol (meth)acrylates containing a hydroxy or ether end group.

23. The composition according to claim 1, wherein the concentration of said graft copolymer in said composition ranges from 0.1 to 50%, relative to the total weight of the composition.

24. The composition according to claim 23, wherein the concentration of said graft copolymer in said composition ranges from 1 to 30%, relative to the total weight of the composition.

25. The composition according to claim 1, wherein said cosmetically or dermatologically acceptable carrier is water, one or more cosmetically acceptable organic solvents or a mixture of water and of one or more cosmetically acceptable organic solvents.

26. The composition according to claim 25, wherein said one or more cosmetically acceptable organic solvent is a $C_1$–$C_4$ lower alcohol.

27. The composition according to claim 1, wherein said graft copolymer is dissolved in or dispersed in said carrier.

28. The composition according to claim 1, wherein said composition further comprises one or more cosmetic additives which are mineral oils, vegetable oils, animal oils, synthetic oils, animal waxes, fossil waxes, vegetable waxes, mineral waxes, synthetic waxes, organic solvents, thickening agents, emollients, antifoam agents, hydrating agents, moisteners, treating agents, antiperspirants, alkalifying agents, acidifying agents, UV-A sunscreens, UV-B sunscreens, broad band sunscreens, dyes, pigments, perfumes, plasticizers, preserving agents, anionic organic polymers, nonionic organic polymers, amphoteric organic polymers or propellent agents.

29. The composition according to claim 1, wherein said composition is a hair-care composition.

30. The composition according to claim 1, wherein said composition is a make-up composition.

31. The composition according to claim 1, wherein said composition is a skin care composition.

32. A process for treating keratinous materials, said process comprising applying to said keratinous materials an amount of a composition as defined in claim 1 effective to impart mechanical and film-forming properties to the keratinous materials.

* * * * *

UNITED STATES PATENT AND TRADEMARK OFFICE
CERTIFICATE OF CORRECTION

PATENT NO. : 6,113,882

DATED : September 5, 2000

INVENTOR(S) : Nathalie MOUGIN et al.

It is certified that error appears in the above-identified patent and that said Letters Patent is hereby corrected as shown below:

IN THE CLAIMS:

Claim 1, col 8, line 29, "dermatologicai" should read --dermatological--

Claim 8, col. 9, line 13, "T'g" should read --Tg--;
line 26, "polycoridensation" should read --polycondensation--.

Signed and Sealed this

Fifteenth Day of May, 2001

*Attest:*

NICHOLAS P. GODICI

*Attesting Officer*     *Acting Director of the United States Patent and Trademark Office*